United States Patent
Koulik et al.

(10) Patent No.: US 6,303,179 B1
(45) Date of Patent: Oct. 16, 2001

(54) METHOD FOR ATTACHMENT OF BIOMOLECULES TO SURFACES THROUGH AMINE-FUNCTIONAL GROUPS

(75) Inventors: Edouard Koulik; Michel Verhoeven, both of Maastricht (NL); Patrick Cahalan; Linda Cahalan, both of Windham, NH (US); Judith Vincent, Beek (NL)

(73) Assignee: Medtronic, INC, Minneapolis, MN (US)

( * ) Notice: Subject to any disclaimer, the term of this patent is extended or adjusted under 35 U.S.C. 154(b) by 0 days.

(21) Appl. No.: 09/245,834

(22) Filed: Feb. 8, 1999

(51) Int. Cl.$^7$ ..................................... A61L 5/103
(52) U.S. Cl. ......................... 427/2.26; 427/2.1; 427/2.24
(58) Field of Search .................. 427/2.1–2.31; 564/488, 414; 525/50; 623/11.11

(56) References Cited

U.S. PATENT DOCUMENTS

| 4,433,030 | | 2/1984 | Tamagawa et al. | ............... 428/476.9 |
|---|---|---|---|---|
| 5,229,172 | * | 7/1993 | Calahan et al. | ...................... 427/536 |
| 5,607,475 | * | 3/1997 | Calahan et al. | ........................ 623/11 |

FOREIGN PATENT DOCUMENTS

| 236 924 A1 | 6/1986 | (DE) . |
|---|---|---|
| 60-69104 | 4/1985 | (JP) . |
| WO 93/14127 | 7/1993 | (WO) . |

OTHER PUBLICATIONS

Sano et al., "Introduction of functional groups onto the surface of polyethylene for protein immobilization," Biomaterials, 14(11), 817–822.*

Tanaka, "Hoffman Reaction of Polyacrylamide: Relationship between Reaction Condition and Degree of Polymerization of Polyvinylamine," Journal of Polymer Science, 17, 1239–1245 (1979).*

"Hofmann Reaction of Polyacrylamide: Relationship between Reaction Condition and Degree of Polymerization of Polyvinylamine," *Journal of Polymer Science*, 17, 1239–1245 (1979).

Lindhout et al., *J. Biomed. Mater. Res.*, 29, 1255–1256.

Lindhout et al., *J. Mater. Sci. Mater. Med.*, 6, 367 (1995).

Nagaty et al., "Graft Polymerization of Vinyl Monomers onto Starch by use of Tetravalent Cerium," *European Polymer Journal*, 16, 343–346 (1980).

Onishi, "Effects of dextran molecular weight on graft copolymerization of dextran–methyl methacrylate," *Polymer*, 21, 819–824 (1980).

Park et al., "Heparin immobilization onto segmented polyurethaneurea surfaces—effect of hydrophilic spacers," *Journal of Biomedical Materials Research*, 22, 977–992 (1988).

Sano et al., "Introduction of functional groups onto the surface of polyethylene for protein immobilization," *Biomaterials*, 14(11), 817–822.

Shioiri, "Degradation Reactions," *Functional Group Interconversion*, chapter 4.4, pp. 795–828.

* cited by examiner

*Primary Examiner*—Dinh X. Nguyen
*Assistant Examiner*—Thomas Barrett
(74) *Attorney, Agent, or Firm*—Thomas F. Woods; Michael J. Jaro; Harold Patton

(57) ABSTRACT

A method of modifying the surface characteristics of a substrate having a surface with an amide-functional polymer thereon. The method involves contacting the amide-functional polymer with a source of hydroxide ions and a source of hypohalite ions at a temperature of at least about 20° C. for a time effective to convert at least a portion of the amide-functional groups to amine-functional groups to form a substrate surface comprising an amine-functional polymer, wherein the hydroxide ions are present in a molar excess relative to the hypohalite ions and at a concentration of no more than about 0.1 M, based on the total volume of the reaction mixture. A biomolecule is attached to the resultant amine-functional polymer.

28 Claims, No Drawings

METHOD FOR ATTACHMENT OF BIOMOLECULES TO SURFACES THROUGH AMINE-FUNCTIONAL GROUPS

FIELD OF THE INVENTION

This invention relates to methods of preparing materials, preferably biocompatible materials, and typically, blood compatible materials. In particular, this invention relates to a method of attaching biomolecules, such as heparin, to the surface of a substrate through amine-functional groups, which are formed from amide-functional groups.

BACKGROUND OF THE INVENTION

The development of vascular grafts and medical devices that contact physiological fluids, particularly blood, is a rapidly developing area of medicine. This has been hampered, however, by the lack of suitable synthetic materials that are stable when contacted with such fluids.

Adverse reactions between materials and blood components are predominant factors limiting the use of synthetic materials that come into contact with physiological fluids. For example, catheters, vascular grafts, and the like, tend to serve as a nidus, or focus, for the formation of thrombi (blood clots). Initial contact of such materials with blood results in deposition of plasma proteins, such as albumin, fibrinogen, immunoglobulin, coagulation factors, and complement components. The adsorption of fibrinogen onto the surface of the material causes platelet adhesion, activation, and aggregation. Other cell adhesive proteins, such as fibronectin, vitronectin, and von Willebrand factor (vWF) also promote platelet adhesion. As a result, the continual use of anticoagulants in conjunction with the introduction of such materials to the body is often necessary.

Furthermore, complement activation occurs when materials are introduced into blood. Adsorption of large amounts of IgG, IgM, and C3b onto surfaces causes activation. Subsequently, complexes may be formed which contribute to undesirable immune responses, such as proteolysis, cell lysis, opsonization, anaphylaxis, and chemotaxis. As a result, these responses render such materials incompatible with the living body.

A number of approaches have been suggested to improve the biocompatibility, and even blood compatibility, of medical devices. Heparinization of polymers is one such approach. In one method, heparin is complexed with a quaternary amine prior to coating the complex onto a polymeric surface. Heparin can also be immobilized onto segmented polyurethane-urea surfaces using hydrophilic poly(ethylene oxide) spacers of different chain lengths, as disclosed in K. D. Park et al., *J. Biomed. Mater. Res.*, 22, 977–992 (1988).

Another heparinization method, which is disclosed in U.S. Pat. No. 5,229,172 (Cahalan et al.), involves initially irradiating a polymeric surface in the presence of an oxygen source and then grafting acrylamide to the irradiated surface using an acrylamide monomer and ceric ions. The grafted acrylamide surface, which can be optionally modified to include pendant functional groups such as amine and carboxyl groups, provides a suitable surface to which a biomolecule can be ionically or covalently bonded. For example, the graft can be subjected to hydrolysis in order to introduce carboxyl groups, to which spacer molecules like ethylenediamine can be coupled, using carbodiimide. To the aminated graft biomolecules such as heparin can be bound using a coupling agnet such as carbodiimide.

Although such conventional methods of attaching biomolecules, particularly heparin, to substrate surfaces have significant advantages, there is still a need for additional methods.

SUMMARY OF THE INVENTION

The present invention provides methods for attaching biomolecules, such as heparin, to substrate surfaces. Preferably, the present invention provides methods for making medical devices having biomolecules attached to (e.g., immobilized on) a substrate surface. The substrate can be made of metal or an organic polymer (i.e., a solid polymeric material).

Significantly, the present invention provides efficient methods by which biomolecules can be attached to a substrate surface containing amidefunctional groups without the need for spacers, such as ethylenediamine, and coupling agents, such as carbodiimide. Rather, the methods of the present invention provide direct conversion of amide (—C(O)NH$_2$) groups to amine (—NH$_3$) groups, which allows for direct attachment of biomolecules.

Specifically, the present invention provides a method of making a medical device having a biomolecule immobilized on a substrate surface. The method includes: providing a substrate having a surface comprising an amide-functional polymer; contacting the amide-functional polymer with a reaction mixture comprising a source of hydroxide ions and a source of hypohalite ions at a temperature of at least about 20° C. for a time effective to convert at least a portion of the amide-functional groups to amine-functional groups to form a substrate surface comprising an amine-functional polymer, wherein the hydroxide ions are present in a molar excess relative to the hypohalite ions and at a concentration of no more than about 0.1 M, based on the total volume of the reaction mixture; and contacting the substrate surface comprising an amine-functional polymer with a biomolecule under conditions effective to immobilize the biomolecule on the substrate surface.

The present invention also provides a method of modifying the surface characteristics of a solid polymeric material, which may or may not form a part of a medical device. The method includes: irradiating a surface of the solid polymeric material; contacting the irradiated surface with an amide-functional ethylenically unsaturated monomer and a source of oxidizing metal ions under conditions effective to graft the monomer to the irradiated surface to form an amide-functional graft polymer thereon; contacting the amide-functional graft polymer with a reaction mixture comprising a source of hydroxide ions and a source of hypohalite ions under conditions effective to convert at least a portion of the amide-functional groups to amine-functional groups to form a solid polymeric material having a surface with an amine-functional graft polymer thereon; and contacting the solid polymeric material having a surface with an amine-functional graft polymer thereon with a biomolecule under conditions effective to immobilize the biomolecule on the surface.

As used herein, a "substrate surface comprising an amide-functional polymer" is a surface of a substrate made of a solid organic polymeric material or metal on which is coated, grafted, or otherwise adhered an organic polymer having at least amide-functional groups. A "substrate surface comprising an amine-functional polymer" is a surface of a substrate made of a solid organic polymeric material or metal on which is coated, grafted, or otherwise adhered an organic polymer having at least amine-functional groups. These polymers can also include other functional groups. The polymers having such functional groups (amide groups, amine groups, etc.) are referred to herein as "functionalized" polymers. Preferably, the functionalized polymer is a graft polymer, and more preferably, a graft hydrogel polymer. Generally, a hydrogel polymer is distinct from a solid polymeric material in the amount of water contained therein. Typically, a solid polymeric material includes less than about 10 wt-% water.

A "medical device" may be defined as a device that has surfaces that contact tissue, blood, or other bodily fluids in the course of their operation, which fluids are subsequently used in patients. This can include, for example, extracorporeal devices for use in surgery such as blood oxygenators, blood pumps, blood sensors, tubing used to carry blood or other devices that contact blood which is then returned to the patient. This can also include endoprostheses implanted in blood contact in a human or animal body such as vascular grafts, stents, pacemaker leads, heart valves, and the like that are implanted in blood vessels or in the heart. This can also include devices for temporary intravascular use such as catheters, guide wires, and the like, which are placed into the blood vessels or the heart for purposes of monitoring or repair.

A "biomolecule" is defined as a biologically active molecule. It can include a variety of drugs (i.e., biologically active agents).

A "biocompatible" material is one that does not generally cause significant adverse reactions (e.g., toxic or antigenic responses) in the body, whether it degrades within the body, remains for extended periods of time, or is excreted whole. Ideally, a biocompatible material will not induce undesirable reactions in the body as a result of contact with bodily fluids or tissue, such as tissue death, tumor formation, allergic reaction, foreign body reaction (rejection), inflammatory reaction, or blood clotting, for example.

DETAILED DESCRIPTION OF THE INVENTION

The biocompatibility of materials used in medical devices, which include implantable materials or materials that are not necessarily implanted but that come into contact with bodily tissues or fluids (e.g., blood), can be improved by attaching, preferably covalently, at least one type of biomolecule, preferably heparin, to a surface through amine-functional groups, which are formed from amide-functional groups. Preferably, the surface is either metal or a solid polymeric material modified to include a functionalized polymer derived from at least one type of amide-functional ethylenically unsaturated monomer, such as acrylamide. The functionalized polymer is preferably a graft polymer, and more preferably, a graft hydrogel polymer.

This amide-functional polymer is converted to an amine-functional polymer by reaction with hydroxide ions and hypohalite ions under conditions that do not degrade the substrate, although the chains of the functionalized polymer may be degraded. These conditions are similar to those of a Hoffman Degradation reaction, although higher temperatures (at least about 20° C.) and lower concentrations of hydroxide ions (no more than about 0.1 M) are used in the methods of the present invention than were previously thought possible for sufficient conversion of amide groups to amine groups without significant polymer degradation.

Temperatures of about 0° C. have typically been used to convert amide groups to amine groups on functionalized polymers in an effort to reduce chain scission reactions. However, it has been found that higher temperatures can be used without significant detrimental effect on the biomolecule loading capacity. Such higher temperatures allow for shorter reaction times, which can lead to lower manufacturing costs. Thus, although degradation of the functionalized polymer can occur, the methods of the present invention provide an acceptable balance between the number of amide groups that are converted to amine groups and the amount of functionalized polymer degraded. Typically, as long as the substrate is homogeneously covered with functionalized polymer (and preferably includes at least about 20 wt-% functionalized polymer), a suitable number of biomolecules can be attached.

Furthermore, it is believed that the functionalized polymer degradation that occurs as a result of the methods of the present invention, may provide an added advantage. Typically, biomolecules attached to graft polymers can leach into the surrounding environment, which may not always be desirable. Thus, the methods of the present invention can remove leachable molecules, such as leachable portions of the functionalized polymer, thereby resulting in a modified substrate surface being less likely to leach during use.

Significantly, this method does not require the use of coupling agents (i.e., activating agents), such as carbodiimide, or spacer molecules, such as ethylenediamine, to attach the biomolecules, although they can be used if desired. Using the methods of the present invention, the extent and severity of adverse reactions between the substrate and bodily fluids, particularly blood, is reduced due to potentially high biomolecule loading capacities and bioactivities.

According to the present invention, a substrate surface is initially modified to include a functionalized polymer, preferably a graft polymer. This can be done using a variety of methods. Preferably, this is done using the methods described in U.S. Pat. Nos. 5,607,475 (Cahalan et al.) and 5,229,172 (Cahalan et al.). These methods describe how to form a graft polymer on substrates made of a metal or a solid polymeric material.

If the substrate includes a metal, prior to forming a graft polymer on the surface, it is preferably coated with a silane compound having pendant vinyl functionality. Such vinylsilanes preferably are of the formula $H_2C=CH-R-Si-X_3$, wherein R is optional and can be a short chain alkyl group, and X is a halogen, methoxy, or ethoxy group. Subsequently, a graft polymer is formed on the vinylsilane coating such that the pendant vinyl functionality of the vinylsilane is incorporated into the graft polymer. This graft polymer is preferably derived from an amide-functional ethylenically unsaturated monomer, such as acrylamide. The polymerization is initiated by a source of oxidizing metal ions, such as ceric ions.

If the substrate includes a solid polymeric material, it is preferably initially irradiated by ionizing radiation and subsequently modified to include a graft polymer. As described above, this graft polymer is preferably derived from an amide-functional ethylenically unsaturated monomer, such as acrylamide, and the polymerization is initiated by a source of oxidizing metal ions, such as ceric ions.

Surface modification of polymeric substrates to include a graft polymer (by first irradiating the polymeric substrate using, for example, corona treatment) is further described in U.S. Pat. No. 5,229,172 (Cahalan et al.). The surface modification of a metal substrate to include a graft polymer (by first coating the metal with a vinylsilane) is further described in U.S. Pat. No. 5,607,475 (Cahalan et al.). Briefly, the surface modification of substrates to include a preferred graft polymer having pendant vinyl functionality is carried out by contacting the substrate (e.g., irradiated polymeric material or metal coated with a vinylsilane) with an aqueous solution of an oxidizing metal (e.g., $Ce^{+4}$) and an amide-functional ethylenically unsaturated monomer (e.g., acrylamide).

The oxidizing metal ions (e.g., $Ce^{+4}$, $Fe^{+3}$, $V^{+5}$, $Co^{+3}$, $Cr^{+6}$, $Fe^{+2}$, $Mg^{+3}$, and $Ni^{+2}$) are typically introduced into the reaction mixture in the form of a salt. For example, ceric ions are preferably introduced into the reaction mixture in the form of one or more ceric salts, such as ceric nitrate, ceric sulfate, ceric ammonium nitrate, ceric ammonium sulfate, ceric ammonium pyrophosphate, ceric iodate, ceric salts of organic acids such as ceric naphthenate and ceric linoleate, and the like. The oxidizing metal ions can be used in various combinations.

The amide-containing ethylenically unsaturated monomers preferably include one or two carbon-carbon double bonds, and more preferably, one carbon-carbon double bond. Examples of amide-containing ethylenically unsaturated monomers include, but are not limited to, acrylamides such as acrylamide and N,N-methylene diacrylamide. These can be used in combination.

In the initial functionalized polymer formation, the amidefunctional ethylenically unsaturated monomer is present in the reaction mixture in an amount of at least about 10 percent by weight (wt-%), and no more than about 50 wt-%, based on the total weight of the reaction mixture. Typically, the concentration of the oxidizing metal ions, which are preferably ceric ions [$Ce^{+4}$], in the reaction mixture is an amount sufficient to initiate the reaction and provide a desired level of graft polymer. Preferably, the concentration is at least about 0.001 molar (M), and no more than about 0.1 M, based on the total volume of the reaction mixture.

According to the present invention, the functionalized polymer having amide-functionality is modified to include amine-functionality using at least one source of hydroxide ions and at least one source of hypohalite ions in a reaction mixture. The reaction mixture typically also includes a liquid carrier such as water, although organic solvents, such as ethanol or other alcohols, can be used alone or in combination with each other or with water. Preferably, the reaction mixture includes water, and the sources of hydroxide and hypohalite ions are soluble in water. The liquid carrier is chosen such that the hydroxide and hypohalite ions are sufficiently soluble to result in effective amide to amine conversion.

Preferably, a source of hydroxide ions includes one or more hydroxide bases and a source of hypohalite ions includes one or more hypohalous acids and/or one or more hypohalite salts. Examples of suitable hydroxide bases include sodium hydroxide and potassium hydroxide. Examples of suitable hypohalous acids and hypohalite salts include, HOCl, HOBr, HOI, and hypohalites of lithium, sodium, and potassium of the formula M(OX), as well as hypohalites of calcium, strontium, and barium of the formula $M(OX)_2$. A particularly preferred hypohalite salt is sodium hypochlorite. In particularly preferred embodiments, the reaction mixture includes sodium hydroxide and sodium hypochlorite. Various combinations of sources of hydroxide ions and hypohalite ions can be used in the conversion of amide groups to amine groups according to the methods of the present invention.

In this reaction, the hydroxide ions are preferably present in the reaction mixture in a molar excess relative to the amount of hypohalite ions. Preferably, the ratio of moles of hydroxide ions to moles of hypohalite ions is at least about 3:1, and more preferably, at least about 5:1. Preferably, the ratio of moles of hydroxide ions to moles of hypohalite ions is no more than about 20:1 and, more preferably, no more than about 10:1.

In preferred embodiments, the reaction mixture includes at least one source of hydroxide ions at a concentration of at least about 0.01 M hydroxide ions, based on the total volume of the reaction mixture, and at least one source of hypohalite ions in an amount of at least about 0.001 M hypohalite ions, based on the total volume of the reaction mixture. Preferably, the hydroxide ions are present at a concentration of no more than about 0.1 M, and the hypohalite ions are present at a concentration of no more than about 0.03 M, based on the total volume of the reaction mixture.

The substrate surface having an amide-functional graft polymer thereon is contacted with (e.g., immersed in or flushed with) the reaction mixture at a sufficient temperature and for a sufficient time to complete the reaction (i.e., conversion of at least a portion of the amide-functional groups to amine-functional groups). Preferably, the reaction time takes at least about minutes, more preferably, at least about 30 minutes, and most preferably, at least about 60 minutes. Preferably, sufficient conversion occurs within about 3 hours, and more preferably, within about 1.5 hours. Significantly, the preferred temperature of the reaction mixture is at least about 20° C., and often no more than about 30° C. Thus, the conversion reaction can be carried out at room temperature (i.e., about 22° C. to about 28° C.). This temperature is significantly higher than that used in conventional methods, which allows for shorter reaction times.

Upon conversion of at least a portion of the amide-functional groups to amine-functional groups, biomolecules can be attached to the substrate surface. Biomolecules useful in the methods of the present invention are those that include moieties reactive with amine-functionality (typically, aldehyde groups), or can be modified to include moieties reactive with amine-functionality. Generally, biomolecules used according to this invention can be, for example: antibacterial and antimicrobial agents; anticoagulant and antithrombotic agents; antiplatelet agents; anti-inflammatories; enzymes; catalysts; hormones; growth factors; drugs; vitamins; antibodies; antigens; nucleic acids; dyes (which act as biological ligands); DNA and RNA; and proteins and peptides. The biomolecules can be synthetically derived or naturally occurring. These biomolecules include, for example, heparin, heparin sulfate, dermatan sulfate, prostaglandin $E_1$ (PGE1), ticlopidine, plasmin, urokinase, and TPA. Other examples are disclosed in U.S. Pat. Nos. 5,229,172 (Cahalan et al.) and 5,607,475 (Cahalan et al.). Various combinations of biomolecules can be used if desired. Heparin, and salts of heparin, such as heparin sulfate, are particularly preferred as they are believed to inhibit the coagulation of blood by interacting with antithrombin III and thrombin to inhibit the conversion of fibrinogen to fibrin.

Biomolecules that do not include groups reactive with amine-functional groups can be modified by a number of methods known to one of skill in the art. One particularly preferred method is an oxidation method involving the use of periodate. The biomolecule, preferably heparin, is contacted with a periodate in a buffered aqueous solution and allowed to react. This controlled oxidation provides a limited number of reactive aldehyde groups per molecule. The periodate is a water-soluble periodate, preferably, an alkali metal periodate, such as sodium periodate. When the biomolecule is heparin, the amount of periodate used is sufficient to react with no more than two of the sugar units in the heparin molecule (i.e., the basic disaccharide residues constituting the structure of the glycosaminoglycan). If the periodate used is sodium periodate and the heparin used is a commercially available injectable form of heparin (e.g., its sodium salt with activity of 160 units/milligram), the weight ratio of heparin to periodate should be about 30:1 or less in order to react with no more than two of the sugar units in the heparin molecule. It will be appreciated by those skilled in the art that the amount of periodate required for other periodate compounds and other forms of heparin can be determined by conventional calculation and empirical tests.

Typically, the reaction between the biomolecule, e.g., heparin, and periodate takes place in an aqueous buffer solution. Generally, buffers having a pH in a neutral to slightly acidic range of about 4.5 to about 8 can be used. A lower pH (e.g., an acetate buffer at pH 4.5) is preferred if a rapid reaction is desired while a more neutral pH (e.g., a phosphate buffer at pH 6.88) is preferred for a slower reaction with a longer storage life. With the acetate buffer at a pH of 4.5, the reaction should proceed for about 3 hours, while with a phosphate buffer at a pH of 6.88, the reaction should proceed for about 16 hours. If desired, the reacted mixture may then be stored prior to use at about 5° C.

The biomolecule can be attached to the amine-functional graft polymer by a number of methods known to one of skill in the art. One particularly preferred method for biomolecules having pendant aldehyde groups is a reduction method involving the use of cyanoborohydride. For example, the reacted mixture described above is diluted and the pH adjusted in order to bring the pH of the mixture to a pH that is favorable for the coupling reaction between the biomolecule and the amine-functional graft polymer. A mild reducing agent, such as sodium cyanoborohydride, is added to the diluted mixture to effect the reduction of the bonds formed between the reactive aldehyde groups on the oxidized biomolecule and the amine-functional graft polymer on the substrate surface. The substrate surface being treated is then contacted with (e.g., immersed in or flushed with) the diluted mixture at a sufficient temperature and for a sufficient time to complete the reaction (i.e., attach the biomolecule). This time can range from about 30 seconds to about 24 hours at temperatures ranging from about 20° C. to about 60° C. For example, at room temperature (i.e., about 20° C. to about 25° C.), the substrate coated with the amine-functional graft polymer can be flushed with a solution of a biomolecule over a period of 30 minutes to 24 hours for effective biomolecule attachment.

The substrates that can be modified by the methods of the present invention include metals or solid polymeric materials that are substantially insoluble in body fluids and that are generally designed and constructed to be placed in or onto the body or to contact fluid of the body. The substrates preferably have the physical properties such as strength, elasticity, permeability, and flexibility required to function for the intended purpose; can be purified, fabricated, and sterilized easily; will substantially maintain their physical properties and function during the time that they remain implanted in or in contact with the body. The substrates used in the present invention may be in a wide variety of shapes or forms, such as powders, plates, strips, films, sheets, fibers, fabrics, filaments, tubing, and cast, extruded or compressed articles, and the like.

Preferred substrates include a solid polymeric material and may include a wide variety of natural or synthetic polymers. Examples include, but are not limited to: polyolefins including polyethylene, polypropylene, polyisobutylene, and ethylene-alpha-olefin copolymers; silicones, such as polydimethylsiloxane; acrylic polymers and copolymers, such as polyacrylate, polymethylmethacrylate (PMMA), and polyethylacrylate; vinyl halide polymers and copolymers, such as polyvinyl chloride; fluoropolymers, such as polytetrafluoroethylene, chlorotrifluoroethylene, fluorinated ethylene-propylene, polyvinylidene fluoride (PVDF), and ethylene tetrafluoroethylene copolymer (ETFE); polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; natural and synthetic rubbers, such as butadiene-styrene copolymers, polyisoprene, synthetic polyisoprene, polybutadiene, butadiene-acrylonitrile copolymers, polychloroprene rubbers, polyisobutylene rubber, ethylene-propylenediene rubber, isobutylene-isoprene copolymers, and polyurethane rubber; polyamides, such as Nylon 66 and polycaprolactam; polyesters, such as polyethylene terephthalate; alkyd resins; formaldehyde-containing resins, such as phenol-formaldehyde resins, urea-formaldehyde resins, and melamine-formaldehyde resins; polycarbonates; polyoxymethylenes; polyimides; polyethers; epoxy resins; polyurethanes; wool; cotton; silk; rayon; rayon-triacetate; cellulosics, such as cellulose acetate, cellulose butyrate, cellulose acetate butyrate, cellulose nitrate, cellulose propionate, cellulose ethers, and carboxymethyl cellulose; polyether block amides; polycarbonates; polyvinyl pyrrolidones; n-butyl cyanoacrylate; polyvinyl alcohols; acrylonitrile butadiene ethylene; styrene acrylonitrile; and the like. Substrates made using these materials can be coated or uncoated, and derivatized or underivatized, prior to being treated with one or more biomolecules. A preferred group of polymers includes those selected from the group of a polyurethane, a polyolefin, a silicone, a fluoropolymer, a polyester, a polyvinyl halide, a polyether, a polyamide, and blends and copolymers thereof. As used herein a copolymer includes terpolymers, tetrapolymers, etc. More preferred polymers include polyurethane or a polyvinyl chloride.

Although polymeric materials are preferred, other suitable substrates include metals such as titanium/titanium alloys, TiNi (shape memory/super elastic), aluminum oxide, platinum/platinum alloys, stainless steels, MP35N, elgiloy, haynes 25, and stellite.

The materials of the present invention include a substrate and a biomolecule attached via the methods of the present invention (via amine-functional graft polymer without the need for other spacer groups or coupling agents) in an amount and orientation effective to provide an improved nonthrombogenic surface relative to the substrate without the biomolecule. The methods of the present invention provide relatively high biomolecule loading capacities (often as high as 50 $\mu$g of biomolecules per square centimeter of modified surface) and bioactivities (often as high as 1.0 International Unit (IU) thrombin (IIa) deactivated per square centimeter of modified surface). For example, polyurethane can be modified with heparin at a level of up to about 35 $\mu$g/cm$^2$, and can demonstrate a bioactivity of up to about 0.7 IU IIa deactivated/cm$^2$.

The contact between blood and a foreign surface initiates a complex process of thrombogenesis that involves platelet adherence, aggregation, and granular release; thrombin generation; and fibrin formation. As a consequence, there are a number of parameters that can be selected as a measure of a material's thrombogenicity. Thus, evaluation of the reactions at the blood-material interface therefore typically involves a multi-parameter (i.e., multi-assay) approach. These assays include, for example, electron microscopy for platelet adhesion, platelet spreading, and thrombin-antithrombin (TAT) assay, as well as others. Any one of these assays can be sufficient to show the improvements resulting from the methods of the present invention.

The blood compatibility of the material of the present invention can be demonstrated by reduced thrombin-antithrombin (TAT) formation upon interaction with blood when compared to the material without the biomolecule attached. By this it is meant that for a substrate to which there is a biomolecule, such as heparin, attached thereto, there is a reduction in the number of thrombin-antithrombin (TAT) complexes formed relative to the same substrate without the biomolecule attached thereto when contacted with human blood. Preferably, this reduction is in an amount of at least about 90%, and more preferably, at least about 95%.

Medical devices in which the biocompatible material of the present invention can be incorporated include, but are not limited to, surgical implants, prostheses, and any artificial part or device which replaces or augments a part of a living body or comes into contact with bodily fluids, particularly blood. The substrates can be in any shape or form including tubular, sheet, rod and articles of proper shape. Various medical devices and equipment usable in accordance with the invention are known in the art. Examples of devices include catheters, suture material, tubing, and fiber membranes. Examples of catheters include central venous catheters, thoracic drain catheters, angioplasty balloon catheters. Examples of tubing include tubing used in extracorporeal circuitry, such as whole blood oxygenators. Examples of membranes include polycarbonate membranes, haemodialysis membranes, and membranes used in diagnostic or biosensor devices. Also included are devices used in diagnosis, as well as polyester yarn suture material such as polyethylene ribbon, and polypropylene hollow fiber membranes.

Further illustrations of medical devices include the following: autotransfusion devices, blood filters, blood pumps, blood temperature monitors, bone growth stimulators, breathing circuit connectors, bulldog clamps, cannulae, grafts, implantable pumps, impotence and incontinence implants, intra-occular lenses, leads, lead adapters, lead connectors, nasal buttons, orbital implants, cardiac insulation pads, cardiac jackets, clips, covers, dialators, dialyzers, disposable temperature probes, domes, drainage products, drapes, ear wicks, electrodes, embolic devices, esophageal stethoscopes, fracture fixation devices, gloves, guide wires, hemofiltration devices, hubs, intra-arterial blood gas sensors, intracardiac suction devices, intrauterine pressure devices, nasal spetal splints, nasal tampons, needles, ophthalmic devices, PAP brushes, periodontal fiber adhesives, pessary, retention cuffs, sheeting, staples, stomach ports, surgical instruments, transducer protectors, ureteral stents, vaginal contraceptives, valves, vessel loops, water and saline bubbles, achtabular cups, annuloplasty ring, aortic/coronary locators, artificial pancreas, batteries, bone cement, breast implants, cardiac materials, such as fabrics, felts, mesh, patches, cement spacers, cochlear implant, defibrillators, generators, orthopedic implants, pacemakers, patellar buttons, penile implant, pledgets, plugs, ports, prosthetic heart valves, sheeting, shunts, umbilical tape, valved conduits, and vascular access devices.

Although the examples described below involve treatment on polymeric films, it is not intended that this invention be so limited.

EXPERIMENTAL EXAMPLES

Example 1

Heparinization of Polyurethane (PU) Film

A) Cleaning and Grafting

Polyurethane (PU) films (PELLETHANE, Bayer, Germany) or tubing samples (PELLETHANE) were cleaned by soaking in isopropyl alcohol for 10 minutes. After drying at 50° C. for 30 minutes, the PU samples were immersed into a water solution containing acrylamide ranging from about 30 wt-% to about 40 wt-%, ammonium ceric nitrate ranging from about 0.003 M to about 0.01 M, and nitric acid ranging from about 0.03 M to about 0.1 M. For each sample, nitrogen gas was bubbled through the solutions for several minutes and then the reaction vessels were sealed. After about 45 minutes to about 75 minutes at room temperature, the PU films were taken out of the reaction vessels and rinsed with water for several minutes.

B) Amination

After rinsing, each grafted sample was placed in a water solution containing sodium hydroxide ranging from about 0.01 M to about 0.1 M and sodium hypochlorite from about 0.001 M to about 0.01 M at room temperature. After about 45 minutes to about 75 minutes, the PU samples were rinsed in water for several minutes.

C) Heparin Coupling

After rinsing, each sample was placed in a periodate heparin solution (typically 1 or 2 mg/ml, pH=4.7, 0.2 M acetate buffer) to which 0.01 wt-% of sodium cyanoborohydride was added. The reaction was carried out for about 30 minutes to about 120 minutes at a temperature ranging from about 20° C. to about 50° C. Periodate heparin solution was prepared by reaction between heparin (5 mg/ml) and sodium periodate (0.16 mg/ml) at room temperature for 16 hours.

Example 2

Heparinization of Polyvinyl Chloride (PVC) Tubing

A) Cleaning and Grafting

Samples of polyvinyl chloride tubing (TIGON, Cole-Parmer Instr., Co., USA) was cleaned by soaking in isopropyl alcohol for 2 minutes. After drying at 50° C. for 15 minutes, each sample of PVC tubing was immersed into a water solution containing acrylamide ranging from about 30 wt-% to about 40 wt-%, ceric ammonium nitrate ranging from about 0.003 M to about 0.01 M, and nitric acid ranging from about 0.03 M to about 0.1 M. Nitrogen gas was bubbled through the solutions for several minutes and then the reaction vessels were sealed. After about 45 minutes to about 75 minutes at 50° C., the samples were taken out of the reaction vessels and rinsed with water for several minutes.

B) Amination

After rinsing, each sample was placed in a water solution containing 0.1 M sodium hydroxide and 0.01 M sodium hypochlorite. After about 75 minutes, each acrylamide-grafted PVC sample was rinsed in water for several minutes.

Heparin Coupling

After rinsing, each sample was placed in a periodate heparin solution (typically 1 or 2 mg/ml, pH=4.7, 0.2 M acetate buffer) to which 0.01 wt-% of sodium cyanoborohydride was added. The reaction was carried out for about 30 minutes to about 120 minutes at a temperature ranging from about 20° C. to about 50° C. Periodate heparin solution was prepared by reaction between heparin (5 mg/ml) and sodium periodate (0.16 mg/ml) at room temperature for 16 hours.

Testing

Antithrombin and thrombin were purified by well known methods (Lindhout et al., *J. Biomed. Mater. Res.*, 29, 1255–1256). The 4th international standard for heparin was obtained from the National Bureau of Standards and Control, London, UK. Chromogenic substrates S2765 and S2238 were obtained from Chromogenix, Sweden. Hepes-buffer consisted of 20 mM Hepes, 0.19 M NaCl, 1.0 mg/ml bovine serum albumin, pH 7.5. Hepes-EDTA buffer was the same as the Hepes-buffer with 20 mM EDTA.

Density of Immobilized Heparin (Heparin Digest)

A sample of modified polyurethane film having a surface area of 5 cm$^2$ was prepared according to the procedure described above. Nitrous acid solution (500 µl of 0.025 M solution) and 250 µl of water were added to the sample and the reaction was carried out for 30 minutes. Amonium sulfamate solution (250 µl of 12.5% weight/volume) was added to the sample and mixed with the nitrous acid solution. A sample of 800 µL of the mixture was collected to which 500 µl of MBTH (3-methyl-2-benzothiazolinone hydrazone hydrochloride, 0.25% weight/volume) was added. After 15 minutes at 50° C., 500 µl of FeCl$_3$ solution was added and the reaction was carried out for an additional 20 minutes at 50° C. After cooling down to room temperature, 2.5 ml of dichloromethane was added and the light absorbency at 660 nm was determined.

Unmodified PU as a control demonstrated no heparin immobilization, whereas PU modified according to the procedure described above demonstrated immobilized heparin in an amount of 35 µg/cm$^2$.

Platelet Adhesion

Blood was drawn from the cubital vein of healthy volunteers into 0.1 vol of 3.8% sodium citrate. Citrated platelet rich plasma (PRP) was prepared by centrifugation for 15 minutes at 250×g at room temperature.

Samples of PU tubing (ID=0.5 cm, length=10 cm) having heparin immobilized on the surface according to the above procedure was exposed to citrated platelet rich plasma (364×10$^9$ platelets/l) at 37° C. for 30 minutes at a flow rate of 250 µl/minute. The non-bound platelets were removed by a wash step with Hepes buffer at the same perfusion speed. The material was then exposed to 1000 µl of 1% Triton solution to lyse the platelets. The number of platelets was determined from the LDH (lactate dehydrogenase) activity in the lysate according to the procedure of T. Lindhout et al., *J. Mater. Sci. Mater. Med.*, 6, 367 (1995).

A calibration curve was constructed from citrated platelet rich plasma diluted with 1% Triton solution. The numbers were corrected for the LDH content of the plasma. These results indicated 50–80% platelet coverage for unmodified polyurethane, whereas polyurethane modified according to the procedure described above demonstrated platelet coverage of 2–20%.

Thrombin Generation Time

PU tubing having heparin immobilized on the surface according to the above procedure was exposed to citrated platelet rich plasma (prepared as described above) for 15 minutes at 37° C. A small aliquot of 1.0 M CaCl$_2$ was added to start the coagulation reaction. The free calcium concentration of recalcified plasma was 4 mM. Samples (3 µL) were removed at timed intervals and assayed for thrombin activity according to the procedure of T. Lindhout et al., *J. Mater. Sci. Mater. Med.*, 6, 367 (1995). The thrombin generation time for unmodified polyurethane was 5–7 minutes, whereas that for polyurethane modified according to the procedure above was 30–40 minutes.

Heparin Bioactivity

Samples of PU with a surface area of 2 cm$^2$ were put in a well plate and hydrated for 10 minutes with a 0.1 N sodium chloride solution, followed by incubation of samples for 15 minutes with Antithrombin III solution in Tris buffer (pH=7). After rinsing, thrombin solution was added to samples in Tris buffer and the incubation was carried out for 10 minutes. The residual thrombin activity in solution was analyzed with the chromogenic substrate S-2238 according to the standard procedure of T. Lindhout et al., *J. Mater. Sci. Mater. Med.*, 6, 367 (1995). This test demonstrated 0.4–0.7 IU IIa deactivated thrombin/cm$^2$.

It will be appreciated by those skilled in the art that while the invention has been described above in connection with particular embodiments and examples, the invention is not necessarily so limited and that numerous other embodiments, examples, uses, modifications and departures from the embodiments, examples and uses are intended to be encompassed by the claims attached hereto. The entire disclosure of each patent and publication cited herein is incorporated by reference, as if each were individually incorporated by reference.

What is claimed is:

1. A method of making a medical device having a biomolecule immobilized on a substrate surface, the method comprising:

providing the substrate, the substrate having a surface comprising an amide-functional polymer;

contacting the amide-functional polymer with a reaction mixture comprising a source of hydroxide ions and a source of hypohalite ions at a temperature of at least about 20° C. for a period of time effective to convert at least a portion of the amide-functional groups to amine-functional groups to form an amine-functional polymer on the substrate surface, the period of time not exceeding about three hours, wherein the hydroxide ions are present in a molar excess relative to the hypohalite ions, and wherein the hydroxide ions are present at a concentration of no more than about 0.1 M, based on the total volume of the reaction mixture; and contacting the substrate surface comprising an amine-functional polymer with a biomolecule under conditions effective to immobilize the biomolecule on the substrate surface.

2. The method of claim 1 wherein the step of contacting the amide-functional polymer comprises immersing the substrate in the reaction mixture.

3. The method of claim 1 wherein the source of hydroxide ions comprises one or more hydroxide bases and the source of hypohalite ions comprises one or more hypohalous acids, one or more hypohalite salts, or mixtures thereof.

4. The method of claim 1 wherein the ratio of moles of hydroxide ions to moles of hypohalite ions is at least about 3:1.

5. The method of claim 4 wherein the ratio of moles of hydroxide ions to moles of hypohalite ions is no more than about 20:1.

6. The method of claim 1 wherein the reaction mixture comprises one or more hydroxide bases at a total concentration of at least about 0.01 M hydroxide ions, based on the total volume of the reaction mixture, and one or more hypohalous acids, one or more hypohalite salts, or mixtures thereof, at a total concentration of at least about 0.001 M to about 0.03 M hypohalite ions, based on the total volume of the reaction mixture.

7. The method of claim 1 wherein the step of contacting the amide-functional polymer comprises contacting it with a reaction mixture comprising a source of hydroxide ions and a source of hypohalite ions in water at a temperature of about 20° C. to about 30° C. for at least about 15 minutes.

8. The method of claim 1 wherein the temperature is within a range of about 20° C. to about 30° C.

9. The method of claim 1 wherein the biomolecule is selected from the group of an antibacterial agent, an antimicrobial agent, an anticoagulant, an antithrombotic agent, an antiplatelet agent, an anti-inflammatory, an enzyme, a catalyst, a hormone, a growth factor, a drugs, a vitamin, an antibody, an antigen, a nucleic acid, a dye, a DNA, an RNA, a protein, a peptide, and mixtures thereof.

10. The method of claim 9 wherein the biomolecule is synthetically derived or naturally occurring.

11. The method of claim 9 wherein the biomolecule comprises heparin or a salt thereof.

12. The method of claim 1 wherein the substrate comprises a solid organic polymer or a metal.

13. The method of claim 12 wherein the substrate comprises a solid organic polymer selected from the group of a polyurethane, a polyolefin, a silicone, a fluoropolymer, a polyester, a polyvinyl halide, a polyether, a polyamide, and blends and copolymers thereof.

14. The method of claim 13 wherein the substrate comprises a polyurethane or a polyvinyl chloride.

15. The method of claim 13 wherein the substrate comprises a solid organic polymer surface having an amide-functional polymer grafted thereto.

16. The method of claim 1 wherein the substrate comprises a metal surface coated with a vinylsilane having an amide-functional polymer grafted thereto.

17. The method of claim 1 wherein the source of hydroxide ions comprises sodium hydroxide, potassium hydroxide, or a mixture thereof.

18. The method of claim 1 wherein the source of hypohalite ions comprises HOCl, LiOCl, NaOCl, KOCl, HOBr, LiOBr, NaOBr, KOBr, HOI, LiOI, NaOI, KOI, $Ca(OCl)_2$, $Sr(OCl)_2$, $Ba(OCl)_2$ $Ca(OBr)_2$, $Sr(OBr)_2$, $Ba(OBr)_2$, $Ca(OI)_2$, $Sr(OI)_2$, $Ba(OI)_2$, or mixtures thereof.

19. The method of claim 1 wherein the surface formed is biocompatible.

20. A method of modifying the surface characteristics of a solid polymeric material, the method comprising:

irradiating a surface of the solid polymeric material;

contacting the irradiated surface with an amide-functional ethylenically unsaturated monomer and a source of oxidizing metal ions under conditions effective to graft the monomer to the irradiated surface to form an amide-functional graft polymer thereon;

contacting the amide-functional graft polymer with a reaction mixture comprising a source of hydroxide ions and a source of hypohalite ions at a temperature of at least about 20° C. for a period of time effective to convert at least a portion of the amide-functional groups to amine-functional groups to form a solid polymeric material having a surface with an amine-functional graft polymer thereon, the period of time not exceeding about three hours, wherein the hydroxide ions are present in a molar excess relative to the hypohalite ions, and wherein the hydroxide ions are present at a concentration of no more than about 0.1 M, based on the total volume of the reaction mixture; and contacting the solid polymeric material having a surface with an amine-functional graft polymer thereon with a biomolecule under conditions effective to immobilize the biomolecule on the surface.

21. The method of claim 20 wherein the source of hydroxide ions comprises one or more hydroxide bases and the source of hypohalite ions comprises one or more hypohalous acids, one or more hypohalite salts, or mixtures thereof.

22. The method of claim 20 wherein the ratio of moles of hydroxide ions to moles of hypohalite ions is at least about 3:1 and no more than about 20:1.

23. The method of claim 20 wherein the temperature is within a range of about 20° C. to about 30° C.

24. The method of claim 20 wherein the biomolecule is heparin or a salt thereof and the ethylenically unsaturated monomer is acrylamide.

25. The method of claim 20 wherein the surface is modified with up to about 50 $\mu$g of the biomolecule per square centimeter.

26. The method of claim 20 wherein the surface formed is biocompatible.

27. A modified polymeric material preparable by the method of claim 20.

28. A medical device preparable by the method of claim 1.

* * * * *

UNITED STATES PATENT AND TRADEMARK OFFICE
CERTIFICATE OF CORRECTION

PATENT NO.    : 6,303,179 B1
DATED         : October 16, 2001
INVENTOR(S)   : Koulik et al.

Page 1 of 1

It is certified that error appears in the above-identified patent and that said Letters Patent is hereby corrected as shown below:

<u>Column 13,</u>
Line 5, change "drugs" to -- drug --.

Signed and Sealed this

Sixth Day of May, 2003

JAMES E. ROGAN
*Director of the United States Patent and Trademark Office*